United States Patent
Bretschneider et al.

(10) Patent No.: US 6,835,847 B2
(45) Date of Patent: Dec. 28, 2004

(54) PHTHALIC ACID DIAMIDE, METHOD FOR THE PRODUCTION THEREOF AND THE USE OF THE SAME AS A PESTICIDE

(75) Inventors: Thomas Bretschneider, Lohmar (DE); Christoph Erdelen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/467,018

(22) PCT Filed: Jan. 25, 2002

(86) PCT No.: PCT/EP02/00809

§ 371 (c)(1),
(2), (4) Date: Aug. 1, 2003

(87) PCT Pub. No.: WO02/062807

PCT Pub. Date: Aug. 15, 2002

(65) Prior Publication Data

US 2004/0077597 A1 Apr. 22, 2004

(30) Foreign Application Priority Data

Feb. 6, 2001 (DE) .......................................... 101 05 169
Mar. 29, 2001 (DE) .......................................... 101 15 406

(51) Int. Cl.[7] ............................. C07F 7/10; A01N 55/00
(52) U.S. Cl. ........................ 556/419; 514/63; 514/770
(58) Field of Search ................. 556/419; 514/63, 514/770

(56) References Cited

U.S. PATENT DOCUMENTS 6,603,044 B1 * 8/2003 Tohnishi et al. ............. 564/154

FOREIGN PATENT DOCUMENTS

EP 0 249 015 12/1987
EP 0 360 417 3/1990
EP 0 919 542 6/1999
EP 1 006 107 6/2000

OTHER PUBLICATIONS

Patent Abstracts of Japan vol. 016, No. 283 (C–0955), Jun. 24, 1992 & JP 04 074187 A (Toshiba Silicone Co Ltd), 9. März 1992 (Mar. 9, 1992).

Tetrahedron Letters 40, (month unavailable) 1999, pp. 4467–4471, William H. Pearson and Roger B. Clark, "Formation and cycloaddition of nonstabilizated N–unsubstituted azomethine ylides from (2–azaallyl)stannanes and (2–azaallyl)silanes".

J. Org. Chem., vol. 28, Jun. 1963, pp. 1496–1498, James U. Lowe, Jr., Takahiko A. Oda, and Robert Evans, "Preparation and Reactions of 1–(Nitroguanyl)aziridines".

Chem. Ind. 37, (month unavailable) 1985, pp. 730–732, Harry R. Urgerer, "Schiffsfarben—eine Spezialität der seenahen Lackindustrie".

* cited by examiner

Primary Examiner—Shailendra Kumar
(74) Attorney, Agent, or Firm—Richard E. L. Henderson

(57) ABSTRACT

The invention relates to novel phthalamides of the formula (I)

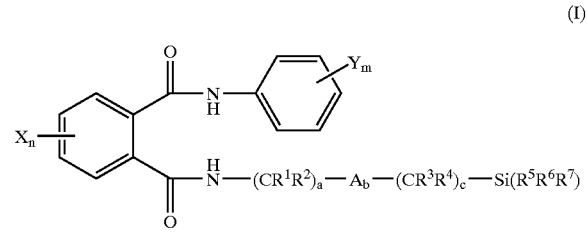

in which disclosure. The invention further relates to a process for preparing these compounds and their use for controlling pests.

25 Claims, No Drawings

PHTHALIC ACID DIAMIDE, METHOD FOR THE PRODUCTION THEREOF AND THE USE OF THE SAME AS A PESTICIDE

This application is a 371 of PCT/EP02/00809, filed Jan. 25, 2002.

The present invention relates to novel phthalamides, to a process for the preparation and to their use as pesticides.

It is already known that numerous phthalamides have insecticidal properties (cf. EP 0 919 542 A and EP 1 006 107 A). However, with respect to their compatibility with plants and efficacy, the known compounds are not always satisfactory. It has now been found that phthalamides which contain a silicon atom in the side chain have very good insecticidal and acaricidal properties and are tolerated well by plants.

This invention, accordingly, provides phthalamides of the formula (I)

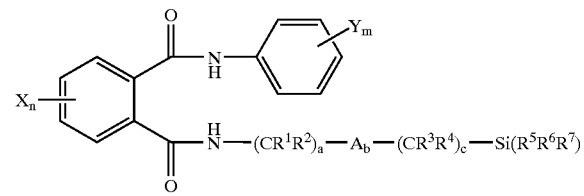

(I)

in which

X and Y independently of one another represent hydrogen, halogen, cyano, nitro, alkyl, halogenoalkyl, alkoxy, halogenoalkoxy, cycloalkyl, halogenocycloalkyl, cycloalkyloxy, halogenocycloalkyloxy, —S(O)$_d$-alkyl, —S(O)$_d$-halogenoalkyl or represent in each case optionally substituted phenyl, phenoxy, heteroaryl or heteroaryloxy, n represents 1, 2, 3 or 4, m represents 1, 2, 3, 4 or 5, $R^1$, $R^2$, $R^3$ and $R^4$ independently of one another represent hydrogen, alkyl, halogenoalkyl or cycloalkyl, $R^5$, $R^6$ and $R^7$ independently of one another represent alkyl or alkoxy, A represents —S(O)$_d$— or oxygen, a represents 1, 2, 3 or 4, with the proviso that the repeat unit —$CR^1R^2$— may have identical or different meanings if a represents 2, 3 or 4, b represents 0 or 1, c represents 0, 1, 2, 3 or 4, with the proviso that the repeat unit —$CR^3R^4$— may have identical or different meanings if c represents 2, 3 or 4, d represents 0, 1 or 2.

Depending on the nature and number of substituents, the compounds of the formula (I) may, if appropriate, be present as geometrical and/or optical isomers, regioisomers and/or configurational isomers or isomer mixtures thereof of varying compositions. What is claimed by the invention are both the pure isomers and the isomer mixtures.

Furthermore, it has been found that the novel compounds of the formula (I) obtained by reacting imides of the formula (II)

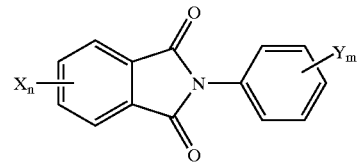

(II)

in which

X, Y, n and m have the meanings given above with silylamines of the formula (III)

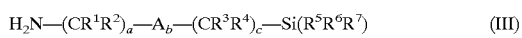

(III)

$H_2N$—$(CR^1R^2)_a$—$A_b$—$(CR^3R^4)_c$—$Si(R^5R^6R^7)$ in which $R^1$, $R^2$, $R^3$, $R^4$, $R^5$, $R^6$, $R^7$, A, a, b and c have the meanings given above, if appropriate in the presence of a diluent.

Finally, it has been found that the compounds of the formula (I) according to the invention have very good insecticidal properties and can be used in both crop protection and in the protection of materials for controlling undesirable pests, such as insects and acarids. Surprisingly, the phthalamides according to the invention, which contain a silicon atom in the side chain, have very good insecticidal- and acaricidal activity and are at the same time tolerated well by plants.

The formula (I) provides a general definition of the phthalamides according to the invention.

X and Y independently of one another preferably represent hydrogen, halogen, cyano, nitro, $C_1$–$C_6$-alkyl, $C_1$–$C_6$-halogenoalkyl, $C_1$–$C_6$-alkoxy, $C_1$–$C_6$-halogenoalkoxy, $C_3$–$C_6$-cycloalkyl, $C_3$–$C_6$-halogenocycloalkyl, $C_3$–$C_6$-cycloalkyloxy, $C_3$–$C_6$-halogenocycloalkyloxy, —S(O)$_d$—$C_1$–$C_6$-alkyl, —S(O)$_d$—$C_1$–$C_6$-halogenoalkyl or represent phenyl, phenoxy, heteroaryl or heteroaryloxy, each of which is optionally mono- to tetrasubstituted by identical or different substituents from the group consisting of halogen, $C_1$–$C_6$-alkyl and $C_1$–$C_6$-halogenoalkyl.

X and Y furthermore independently of one another preferably represent phenyl, phenoxy, heteroaryl or heteroaryloxy, each of which is optionally mono- to tetrasubstituted by identical or different substituents from the group consisting of $C_1$–$C_6$-alkoxy, $C_1$–$C_6$-halogenoalkoxy, $C_1$–$C_6$-alkylthio and $C_1$–$C_6$-halogenoalkylthio.

n preferably represents 1, 2 or 3.

m preferably represents 1, 2, 3 or 4.

$R^1$, $R^2$, $R^3$ and $R^4$ independently of one another preferably represent hydrogen, $C_1$–$C_6$-alkyl, $C_1$–$C_6$-halogenoalkyl or $C_3$–$C_6$-cycloalkyl.

$R^5$, $R^6$ and $R^7$ independently of one another preferably represent $C_1$–$C_6$-alkyl or $C_1$–$C_6$-alkoxy.

A preferably represents —S(O)$_d$— or oxygen.

a preferably represents 1, 2, 3 or 4, with the proviso, that the repeat unit —$CR^1R^2$— may have identical or different meanings if a represents 2, 3 or 4.

b preferably represents 0 or 1.

c preferably represents 0, 1, 2, 3 or 4, with the proviso that the repeat unit —$CR^3R^4$— may have identical or different meanings if c represents 2, 3 or 4.

d preferably represents 0, 1 or 2.

X and Y independently of one another particularly preferably represents hydrogen, fluorine, chlorine, bromine, iodine, cyano, nitro, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_3$–$C_6$-cycloalkyl, —S(O)$_d$—$C_1$–$C_4$-alkyl, —S(O)$_d$—$C_1$–$C_4$-halogenoalkyl having 1 to 9 fluorine, chlorine and/or bromine atoms.

Y furthermore particularly preferably represents phenyl, phenoxy, 5- or 6-membered heteroaryl or heteroaryloxy having 1 to 4 heteroatoms including 0 to 4 nitrogen atoms, 0 to 2 nonadjacent oxygen atoms and/or 0 to 2 nonadjacent sulphur atoms (in particular furyl, furyloxy, thienyl, thienyloxy, pyrrolyl, pyrrolyloxy, tetrazolyl, pyridyl, pyridyloxy, pyrimidinyl, pyrimidinyloxy, pyridazinyl, pyridazinyloxy, pyrazinyl, pyrazinyloxy), each of which is optionally mono- to tetrasubstituted by identical or different substituents from the group consisting of fluorine, chlorine, bromine, iodine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms, $C_1$–$C_4$-alkylthio, $C_1$–$C_4$-halogenoalkylthio having 1 to 9 fluorine, chlorine and/or bromine atoms.

n particularly preferably represents 1 or 2.

m particularly preferably represents 1, 2 or 3.

$R^1$, $R^2$, $R^3$ and $R^4$ independently of one another particularly preferably represents hydrogen, $C_1$–$C_4$-alkyl, $C_1$–$C_4$-halogenoalkyl having 1 to 9 fluorine, chlorine and/or bromine atoms or $C_3$–$C_6$-cycloalkyl.

$R^5$, $R^6$ and $R^7$ independently of one another particularly preferably represents $C_1$–$C_3$-alkyl or $C_1$–$C_3$-alkoxy.

A particularly preferably represents —S(O)$_d$— or oxygen.

a particularly preferably represents 1, 2 or 3, with the proviso that the repeat unit —CR$^1$R$^2$— may have identical or different meanings if a represents 2 or 3.

b particularly preferably represents 0 or 1.

c particularly preferably represents 0, 1, 2 or 3, with the proviso that the repeat unit —CR$^3$R$^4$— may have identical or different meanings if c represents 2 or 3.

d particularly preferably represents 0, 1 or 2.

X very particularly preferably represents chlorine, bromine, iodine.

Y very particularly preferably represents methyl, ethyl, n-propyl, isopropyl, trifluoromethyl, pentafluoroethyl, n-heptafluoropropyl, isoheptafluoropropyl, trifluoromethoxy or —OCF$_2$CF$_2$H.

Y furthermore very particularly preferably represents phenoxy, pyridinyloxy or tetrazolyl, each of which is mono- to trisubstituted by identical or different substituents from the group consisting of fluorine, chlorine, bromine, iodine, methyl, ethyl, n-propyl, isopropyl, n-butyl, isobutyl, sec-butyl, tert-butyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —OCF$_3$, —OCHF$_2$, —OCF$_2$CF$_2$H, —SCF$_3$, —SCHF$_2$.

n very particularly preferably represents 1.

m very particularly preferably represents 2.

$R^1$, $R^2$, $R^3$ and $R^4$ independently of one another very particularly preferably represent hydrogen, methyl or ethyl.

$R^5$, $R^6$ and $R^7$ independently of one another very particularly preferably represents methyl, ethyl, methoxy or ethoxy.

A very particularly preferably represents —S(O)$_d$— or oxygen.

a very particularly preferably represents 1, 2 or 3, with the proviso that the repeat unit —CR$^1$R$^2$— may have identical or different meanings if a represents 2 or 3.

b very particularly preferably represents 0 or 1.

c very particularly preferably represents 0, 1 or 2, with the proviso that the repeat unit —CR$^3$R$^4$— may have identical or different meanings if c represents 2.

d very particularly preferably represents 0, 1 or 2.

Very particular preference is furthermore given to compounds of the formula (I-a)

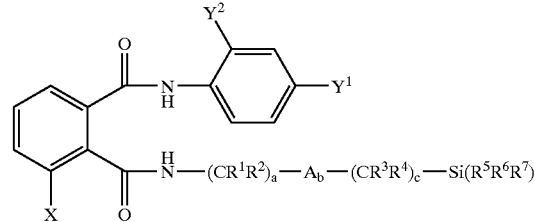

(I-a)

in which $Y^1$ and $Y^2$ independently of one another have the meanings of the radical Y given above, A represents sulphur or oxygen, b represents 0 or 1 and X, $R^1$, $R^2$, $R^3$, $R^4$, $R^5$, $R^6$, $R^7$, a and c have the meanings given above.

Very particular preference is furthermore given to compounds of the formula (I-b)

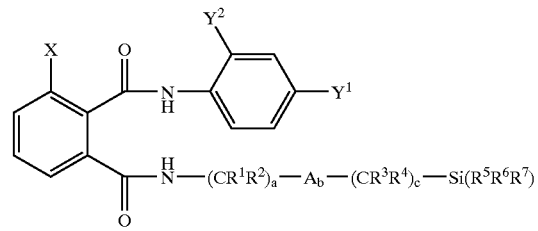

(I-b)

in which $Y^1$ and $Y^2$ independently of one another have the meanings of the radical Y given above, A represents sulphur or oxygen, b represents 0 or 1 and X, $R^1$, $R^2$, $R^3$, $R^4$, $R^5$, $R^6$, $R^7$, a and c have the meanings given above.

Very particular preference is furthermore given to compounds of the formulae (I-a) and the formula (I-b), in which A represents SO or SO$_2$.

Very particular preference is furthermore given to compounds of the formulae (I-a) and the formula (I-b), in which $Y^1$ and $Y^2$ independently of one another have the preferred, particularly preferred or very particularly preferred meanings of the radical Y given above, A represents S(O)$_d$ or oxygen, b represents 0 or 1, d represents 0, 1 or 2 and X, $R^1$, $R^2$, $R^3$, $R^4$, $R^5$, $R^6$, $R^7$, a and c have the preferred, particularly preferred or very particularly preferred meanings given above.

Preference is furthermore given to compounds of the formula (I) in which $R^5$, $R^6$ and $R^7$ each represent methyl.

Preference is furthermore given to compounds of the formula (I) in which A represents S, SO or $SO_2$.

Preference is furthermore given to compounds of the formulae (I-a) and the formula (I-b) in which $Y^1$ represents $C_1$–$C_4$-alkyl, preferably trifluoromethyl, pentafluoroethyl, n-heptafluoropropyl, isoheptafluoropropyl, particularly preferably isoheptafluoropropyl.

Preference is furthermore given to compounds of the formulae (I-a) and the formula (I-b) in which $Y^2$ represents methyl.

Saturated hydrocarbon radicals, such as alkyl, can in each case be straight-chain or branched as far as this is possible, including in combination with heteroatoms, such as, for example, alkoxy.

However, the general or preferred radical definitions or illustrations given above can also be combined with one another as desired, i.e. between the respective ranges and preferred ranges. They apply both to the end products and, correspondingly, to the precursors and intermediates.

Using 4-chloro-2-{2-methyl-4-[1,2,2,2-tetrafluoro-1-(trifluoromethyl)ethyl]phenyl}-1H-isoindole-1,3(2H)-dione and 1-{[(trimethylsilyl)methyl]sulphanyl}-2-propanamine as starting materials, the cause of the process according to the invention can be illustrated by the equation below.

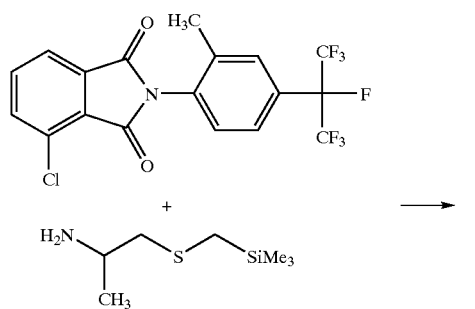

+

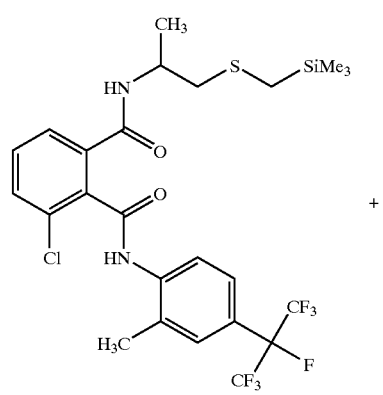

+

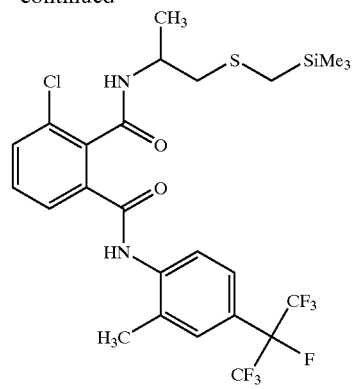

The formula (II) provides a general definition of the imides required as starting materials for carrying out the process according to the invention. In this formula, X, Y, n and m preferably, particularly preferably and very particularly preferably have those meanings which have already been mentioned in connection with the description of the compounds of the formula (I) according to the invention as being preferred, particularly preferred, etc., for these radicals.

Imides of the formula (II) are known (cf. EP 0 919 542 A and EP 1 006 107 A).

The formula (III) provides a general definition of the silylamines required as starting materials for carrying out the process according to the invention. In this formula, $R^1$, $R^2$, $R^3$, $R^4$, $R^5$, $R^6$, $R^7$, A, a, b and c preferably, particularly preferably and very particularly preferably have those meanings which have already been mentioned in connection with the description of the compounds of the formula (I) according to the invention as being preferred, particularly preferred, etc., for these radicals.

Some of the silylamines of the formula (III) are known (cf. Tetrahedron Lett. 1999, 40, 4467).

Silylamines of the formula (III-a)

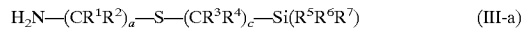

$$H_2N-(CR^1R^2)_a-S-(CR^3R^4)_c-Si(R^5R^6R^7) \qquad (III\text{-}a)$$

in which $R^1$, $R^2$, $R^3$, $R^4$, $R^5$, $R^6$, $R^7$, a and c have the meanings given above, can be prepared, for example, by reacting aziridines of the formula (IV)

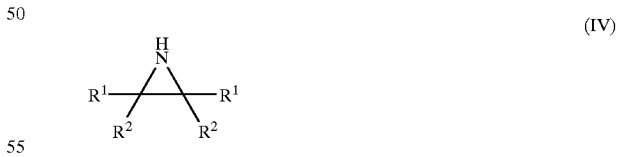

(IV)

in which $R^1$ and $R^2$ have the meanings given above with thiols of the formula (V)

$$HS-(CR^3R^4)_c-Si(R^5R^6R^7) \qquad (V)$$

in which $R^3$, $R^4$, $R^5$, $R^6$, $R^7$ and c have the meanings given above, if appropriate in the presence of a diluent (for example, methanol) (cf. J. Org. Chem. 1963, 28, 1496).

Suitable diluents for carrying out the process according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane; carboxylic acids, such as formic acid or acetic acid. Particularly preferably, the process is carried out in acetic acid or in the absence of a diluent.

When carrying out the process according to the invention, the reaction temperatures can in each case be varied within a relatively wide range. In general, the process is carried out at temperatures between 20° C. and 150° C., preferably between 50° C. and 120° C.

When carrying out the process according to the invention, in general from 1 to 3 mol of a compound of the formula (III) are employed per mole of the compound of the formula (II). However, it is also possible to employ the reaction components in other ratios. Work-up is carried out by customary methods. In general, the reaction mixture is concentrated, the residue is taken up in a suitable solvent and the product is freed of any impurities that may still be present by chromatography.

All processes according to the invention are generally carried out under atmospheric pressure. However, in each case it is also possible to operate under elevated or reduced pressure.

The active compounds according to the invention are suitable for controlling animal pests, in particular insects, arachnids and nematodes, which are encountered in agriculture, in forestry, in the protection of stored products and of materials, and in the hygiene sector, and are well tolerated by plants and have favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus sirmilis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds according to the invention with extenders, that is liquid solvents and/or solid carriers, optionally with the use of surfactants, that is emulsifiers and/or dispersants and/or foam-formers.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are: for example, ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example, lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be used in commercially available formulations and in the use forms prepared from these formulations as a mixture with other active compounds which are also known, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly suitable co-components are, for example, the following compounds:

Fungicides aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanato-methyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one, Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides nematicides abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfhan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyclopene, cyclopene, cyclopropthrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., eprinomectin, esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin, nuclear polyhedrosis viruses,
lambda-cyhalothrin, lufenuron,
malathion, mecarbam, metaldehyde, methamidophos, *Metharhizium anisopliae, Metharhizium flavoviride*,
methidathion, methiocarb, methomyl, methoxyfenozide, metolcarb, metoxadiazone, mevinphos, milbemectin, milbemycin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulphotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl)-3-furanyl]-methyl3-[(dihydro-2-oxo-3(2H)-furanylidene)-methyl]-2,2-dimethyl-cyclopropanecarboxylate,
(3-phenoxyphenyl)-methyl 2,2,3,3-tetramethylcyclo-propanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl) phenyl]-4,5-dihydro-oxazole,
2-(acetyloxy)-3-dodecyl-1,4-naphthalenedione,
2-chloro-N-[[[4-(1-phenylethoxy)-phenyl]-amino]-carbonyl]-benzamide,
2-chloro-N-[[[4-(2,2-dichloro-1,1-difluoroethoxy)-phenyl]-amino]-carbonyl]-benzamide,
3-methylphenyl propylcarbamate.
4-[4-(4-ethoxyphenyl)-4-methylpentyl]-1-fluoro-2-phenoxy-benzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyridazinone,
4-chloro-5-[(6-chloro-3-pyridinyl)methoxy]-2-(3,4-dichlorophenyl)-3(2H)-pyridazinone,
*Bacillus thuringiensis* strain EG-2348,
[2-benzoyl-1-(1,1-dimethylethyl)-hydrazinobenzoic acid,
2,2-dimethyl-3-(2,4-dichlorophenyl)-2-oxo-1-oxaspiro[4.5] dec-3-en-4-yl butanoate,
[3-[(6-chloro-3-pyridinyl)methyl]-2-thiazolidinylidene]-cyanamide,
dihydro-2-(nitromethylene)-2H-1,3-thiazine-3(4H)-carboxaldehyde,
ethyl [2-[[1,6-dihydro-6-oxo-1-(phenylmethyl)-4-pyridazinyl]oxy]ethyl]-carbamate,
N-(3,4,4-trifluoro-1-oxo-3-butenyl)-glycine,
N-(4-chlorophenyl)-3-[4-(difluoromethoxy)phenyl]-4,5-dihydro-4-phenyl-1H-pyrazole-1-carboxamide,
N-[(2-chloro-5-thiazolyl)methyl]-N'-methyl-N"-nitro-guanidine,
N-methyl-N'-(1-methyl-2-propenyl)-1,2-hydrazine-dicarbothioamide, N-methyl-N'-2-propenyl-1,2-hydrazinedicarbothioamide,
O,O-diethyl [2-(dipropylamino)-2-oxoethyl]-ethylphosphoramidothioate It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having specific properties ("traits") which can be obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example, by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants against fungi, bacteria and viruses by systemic acquired resistance (SAR), systemin, phytoalexihs, elicitovs and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example, the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example, maize, cotton, soya beans), KnockOut® (for example, maize), StarLink® (for example, maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example, maize, cotton, soya bean), Liberty Link® (tolerance to phosphinotricin, for example oilseed rape), IMI® (tolerance to imidazolinones) and STS® (tolerance to sulphonylureas, for example, maize). Herbicide-resistant plants (plants bred in a conventional manner for herbicide tolerance) which may be mentioned include the varieties sold under the name Clearfield® (for example, maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp. From the order of the Heteropterida, for example, *Cimex* spp., *Triatoma* spp., *Rhodnius* spp. and *Panstrongylus* spp. From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks such as, for example, *Amblyomma hebraeum*, against parasitic flies such as, for example, *Lucilia cuprina* and against flies, such as, for example, *Ctenocephalides felis*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reductions in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example, powders, emulsions, free-flowing compositions), which comprise the active compounds according to the invention in an amount of 1 to 80% by weight, directly or after 100 to 10000-fold dilution, or they can be used as a chemical bath.

It has furthermore been found that the compounds according to the invention have a strong insecticidal action against insects which destroy industrial materials.

The following insects may be mentioned as examples and as preferred—but without limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are especially preferably materials to be protected from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes. The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and, if appropriate, dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and, if appropriate, an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloro-naphthalene, are used.

The organic oily or oil-like solvents of low volatility which have an evaporation number above 35 and a flash-point above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl (bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Avicularidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Droso-* phila spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

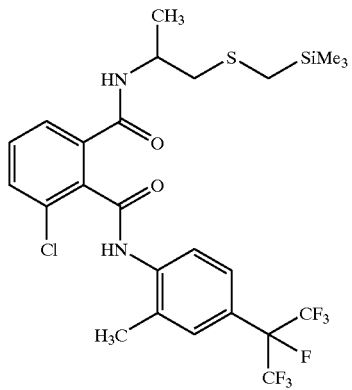

Isomer 1

+

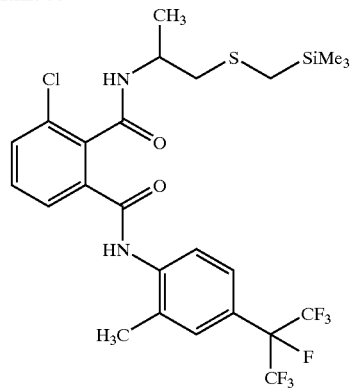

Isomer 2

At 100° C., 0.50 g (1.137 mmol) of 4-chloro-2-{2-methyl-4-[1,2,2,2-tetrafluoro-1-(trifluoromethyl)ethyl]phenyl}-1H-isoindole-1,3(2H)-dione and 0.222 g (1.251 mmol) of 1-{[(trimethylsilyl)methyl]sulphanyl}-2-propanamine are stirred in the absence of a solvent for 1 h. The crude product is then purified by silica gel column chromatography (mobile phase: dichloromethane).

Isomer 1

3-Chloro-$N^2$-{2-methyl-4-[1,2,2,2-tetrafluoro-1-(trifluoromethyl)ethyl]phenyl}-$N^1$-(1-methyl-2-{[(trimethylsilyl)methyl]sulphanyl}ethyl)phthalamide

| | |
|---|---|
| Yield: | 0.12 g (15% of theory) |
| m.p.: | 159–160° C. |
| HPLC: | log P (pH 2.3) = 5.38 |
| $^1$H-NMR (CD$_3$CN): | δ = 0 (9H), 1.15 (d, 3H), 1.74 (m, 2H), 2.32 (s, 3H), 2.55 (m, 1H), 2.65 (m, 1H), 4.14 (m, 1H), 6.85 (m, 1H), 7.55 (m, 5H), 8.05 (m, 1H), 8.30 (m, 1H) ppm. |

Isomer 2

3-Chloro-$N^1$-{2-methyl-4-[1,2,2,2-tetrafluoro-1-(trifluoromethyl)ethyl]phenyl}-$N^2$-(1-methyl-2-{[(trimethylsilyl)methyl]sulphanyl}ethyl)phthalamide

| | |
|---|---|
| Yield: | 0.20 g (27% of theory) |
| m.p.: | 161–162° C. |
| HPLC | log P (pH 2.3) = 5.56 |
| $^1$H-NMR (CD$_3$CN): | δ = 0 (9H), 1.15 (d, 3H), 1.75 (m, 2H), 2.35 (s, 3H), 2.5 (m, 1H), 2.65 (m, 1H), 4.15 (m, 1H), 6.95 (m, 1H), 7.55 (m, 3H), 7.65 (m, 1H), 7.75 (m, 1H), 8.15 (m, 1H), 8.55 (m, 1H) ppm. |

Example 2

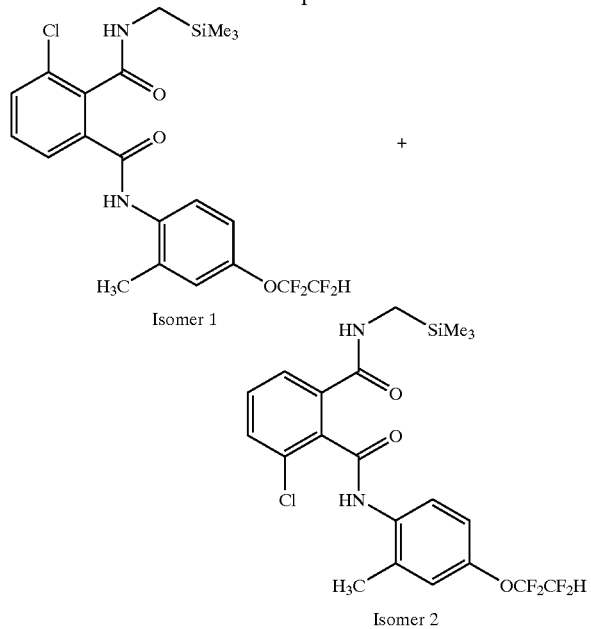

Isomer 1

Isomer 2

0.50 g (1.29 mmol) of 4-chloro-2-[2-methyl-4-(1,1,2,2-tetrafluoroethoxy)phenyl]-1H-isoindole-1,3(2H)-dione and 0.38 g (3.65 mmol) of trimethylsilylmethylamine are heated at reflux for 16 h. The reaction mixture is then concentrated under reduced pressure and the crude product is triturated with diisopropyl ether.

Isomer Mixture

3-Chloro-$N^1$-[2-methyl-4-(1,1,2,2-tetrafluoroethoxy)phenyl]-$N^2$-[(trimethylsilyl)methyl]phthalamide (Isomer 1) and 3-chloro-$N^2$-[2-methyl-4-(1,1,2,2-tetrafluoroethoxy)phenyl]-$N^1$-[(trimethylsilyl)methyl]phthalamide (Isomer 2)

| | |
|---|---|
| Yield: | 0.55 g (56% of theory) |
| HPLC: | log P (pH 2.3) = 3.59 and 3.69 |
| $^1$H-NMR (CD$_3$CN): | δ = 0.1 (9H), 2.25 (s, 3H), 2.75 (s, 2H), 6.12 (m, 1H), 6.7–8.5 (m, 8H) ppm. |

Example 3

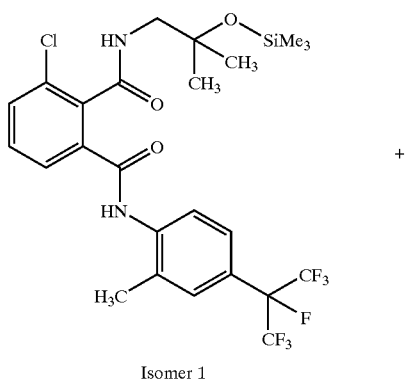

Isomer 1

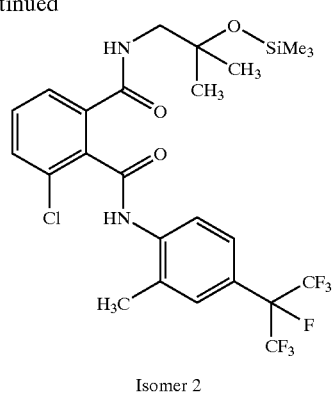

Isomer 2

0.80 g (1.819 mmol) of 4-chloro-2-{2-methyl-4-[1,2,2,2-tetrafluoro-1-(trifluoromethyl)ethyl]phenyl}-1H-isoindole-1,3(2H)-dione and 0.587 g (3.639 mmol) of 2-methyl-2-[(trimethylsilyl)oxy]-1-propanamine are stirred at 100° C. in the absence of a solvent for 1 h. The crude product is then purified by silica gel column chromatography (mobile phase: dichloromethane).

Isomer 1

3-Chloro-$N^1$-{2-methyl-4-[1,2,2,2-tetrafluoro-1-(trifluoromethyl)ethyl]phenyl}-$N^2$-{2-methyl-2-[(trimethylsilyl)oxy]propyl}phthalamide

| | |
|---|---|
| Yield: | 0.42 g (23% of theory) |
| m.p.: | 144–145° C. |
| HPLC: | log P (pH 2.3) = 3.11 |
| $^1$H-NMR (CD$_3$CN): | δ = 0 (9H), 1.15 (s, 6H), 2.3 (s, 3H), 3.2 (m, 2H), 6.70–8.50 (m, 8H). |

Isomer 2

3-Chloro-$N^2$-{2-methyl-4-[1,2,2,2-tetrafluoro-1-(trifluoromethyl)ethyl]phenyl}-$N^1$-{2-methyl-2-[(trimethylsilyl)oxy]propyl}phthalamide

| | |
|---|---|
| Yield: | 0.27 g (22% of theory) |
| m.p.: | 163–164° C. |
| HPLC: | log P (pH 2.3) = 3.19 |
| $^1$H-NMR (CD$_3$CN): | δ = 0 (9H), 1.1 (s, 3H), 1.15 (s, 3H), 2.3 (s, 3H), 3.25 (m, 2H), 6.95 (m, 1H), 7.45 (m, 3H), 7.60 (m, 2H), 7.95 (m, 1H), 8.35 (m, 1H) ppm. |

The following compounds can be obtained according to one of Examples 1 to 3:

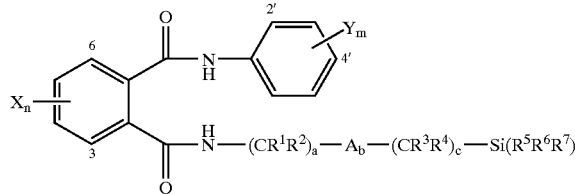

| No. | X | Y | —(CR¹R²)ₐ—Aᵦ—(CR³R⁴)꜀—Si(R⁵R⁶R⁷) | log P (pH 2.3) |
|---|---|---|---|---|
| 4 | 3-Cl | 2'-Me, 4'-i-$C_3F_7$ | —$CH_2SiMe_3$ | 4.72 |
| 5 | 6-Cl | 2'-Me, 4'-i-$C_3F_7$ | —$CH_2SiMe_3$ | 4.58 |
| 6 | 3-Cl | 2'-Me, 4'-$OCF_3$ | —$CH_2SiMe_3$ | |
| 7 | 6-Cl | 2'-Me, 4'-$OCF_3$ | —$CH_2SiMe_3$ | |
| 8 | 3-Cl | 2'-Me, 4'-i-$C_3F_7$ | —$(CH_2)_3$—$Si(OMe)_3$ | |
| 9 | 6-Cl | 2'-Me, 4'-i-$C_3F_7$ | —$(CH_2)_3$—$Si(OMe)_3$ | |
| 10 | 3-Cl | 2'-Me, 4'-$OCF_3$ | —$(CH_2)_3$—$Si(OMe)_3$ | |
| 11 | 6-Cl | 2'-Me, 4'-$OCF_3$ | —$(CH_2)_3$—$Si(OMe)_3$ | |
| 12 | 3-Cl | 2'-Me, 4'-i-$C_3F_7$ | —CH(Me)—$CH_2$—S—$CH_2$—$SiMe(OEt)_2$ | |
| 13 | 6-Cl | 2'-Me, 4'-i-$C_3F_7$ | —CH(Me)—$CH_2$—S—$CH_2$—$SiMe(OEt)_2$ | |
| 14 | 3-Cl | 2'-Me, 4'-$OCF_3$ | —CH(Me)—$CH_2$—S—$CH_2$—$SiMe(OEt)_2$ | |
| 15 | 6-Cl | 2'-Me, 4'-$OCF_3$ | —CH(Me)—$CH_2$—S—$CH_2$—$SiMe(OEt)_2$ | |
| 16 | 3-I | 2'-Me, 4'-i-$C_3F_7$ | —CH(Me)—$CH_2$—S—$CH_2$—$SiMe_3$ | 5.69 |
| 17 | 6-I | 2'-Me, 4'-i-$C_3F_7$ | —CH(Me)—$CH_2$—S—$CH_2$—$SiMe_3$ | 5.46 |
| 18 | 3-I | 2'-Me, 4'-$OCF_3$ | —CH(Me)—$CH_2$—S—$CH_2$—$SiMe_3$ | |
| 19 | 6-I | 2'-Me, 4'-$OCF_3$ | —CH(Me)—$CH_2$—S—$CH_2$—$SiMe_3$ | |
| 20 | 3-I | 2'-Me, 4'-i-$C_3F_7$ | —$C(Me)_2$—$CH_2$—S—$CH_2$—$SiMe_3$ | |
| 21 | 6-I | 2'-Me, 4'-i-$C_3F_7$ | —$C(Me)_2$—$CH_2$—S—$CH_2$—$SiMe_3$ | |
| 22 | 3-I | 2'-Me, 4'-i-$C_3F_7$ | —$C(Me)_2$—$CH_2$—SO—$CH_2$—$SiMe_3$ | |
| 23 | 6-I | 2'-Me, 4'-i-$C_3F_7$ | —$C(Me)_2$—$CH_2$—SO—$CH_2$—$SiMe_3$ | |
| 24 | 3-I | 2'-Me, 4'-i-$C_3F_7$ | —$C(Me)_2$—$CH_2$—$SO_2$—$CH_2$—$SiMe_3$ | |
| 25 | 6-I | 2'-Me, 4'-i-$C_3F_7$ | —$C(Me)_2$—$CH_2$—$SO_2$—$CH_2$—$SiMe_3$ | |
| 26 | 3-Br | 2'-Me, 4'-i-$C_3F_7$ | —$C(Me)_2$—$CH_2$—S—$CH_2$—$SiMe_3$ | |
| 27 | 6-Br | 2'-Me, 4'-i-$C_3F_7$ | —$C(Me)_2$—$CH_2$—S—$CH_2$—$SiMe_3$ | |
| 28 | 3-Br | 2'-Me, 4'-i-$C_3F_7$ | —$C(Me)_2$—$CH_2$—SO—$CH_2$—$SiMe_3$ | |
| 29 | 6-Br | 2'-Me, 4'-i-$C_3F_7$ | —$C(Me)_2$—$CH_2$—SO—$CH_2$—$SiMe_3$ | |
| 30 | 3-Br | 2'-Me, 4'-i-$C_3F_7$ | —$C(Me)_2$—$CH_2$—$SO_2$—$CH_2$—$SiMe_3$ | |
| 31 | 6-Br | 2'-Me, 4'-i-$C_3F_7$ | —$C(Me)_2$—$CH_2$—$SO_2$—$CH_2$—$SiMe_3$ | |
| 32 | 3-Cl | 2'-Me, 4'-i-$C_3F_7$ | —$C(Me)_2$—$CH_2$—S—$CH_2$—$SiMe_3$ | |
| 33 | 6-Cl | 2'-Me, 4'-i-$C_3F_7$ | —$C(Me)_2$—$CH_2$—S—$CH_2$—$SiMe_3$ | |
| 34 | 3-Cl | 2'-Me, 4'-i-$C_3F_7$ | —$C(Me)_2$—$CH_2$—SO—$CH_2$—$SiMe_3$ | |
| 35 | 6-Cl | 2'-Me, 4'-i-$C_3F_7$ | —$C(Me)_2$—$CH_2$—SO—$CH_2$—$SiMe_3$ | |
| 36 | 3-Cl | 2'-Me, 4'-i-$C_3F_7$ | —$C(Me)_2$—$CH_2$—$SO_2$—$CH_2$—$SiMe_3$ | |
| 37 | 6-Cl | 2'-Me, 4'-i-$C_3F_7$ | —$C(Me)_2$—$CH_2$—$SO_2$—$CH_2$—$SiMe_3$ | |
| 38 | 3-I | 2'-Me, 4'-O-(4-$CF_3$-phenyl) | —CH(Me)—$CH_2$—S—$CH_2$—$SiMe_3$ | 5.55 |
| 39 | 6-I | 2'-Me, 4'-O-(4-$CF_3$-phenyl) | —CH(Me)—$CH_2$—S—$CH_2$—$SiMe_3$ | 5.39 |
| 40 | 3-Cl | 2'-Me, 4'-O-(4-$CF_3$-phenyl) | —CH(Me)—$CH_2$—S—$CH_2$—$SiMe_3$ | 5.41 |
| 41 | 6-Cl | 2'-Me, 4'-O-(4-$CF_3$-phenyl) | —CH(Me)—$CH_2$—S—$CH_2$—$SiMe_3$ | 5.26 |
| 42 | 3-I | 2'-Me, 4'-[2-($C(CH_3)_3$)-tetrazol-5-yl] | —CH(Me)—$CH_2$—S—$CH_2$—$SiMe_3$ | 4.98 |
| 43 | 6-I | 2'-Me, 4'-[2-($C(CH_3)_3$)-tetrazol-5-yl] | —CH(Me)—$CH_2$—S—$CH_2$—$SiMe_3$ | 4.70 |

-continued

| No. | X | Y | —(CR¹R²)ₐ—Aᵦ—(CR³R⁴)_c—Si(R⁵R⁶R⁷) | log P (pH 2.3) |
|---|---|---|---|---|
| 44 | 3-I | 2'-Me, 4'-O-(3-Cl-5-CF₃-pyridin-2-yl) | —CH(Me)—CH₂—S—CH₂—SiMe₃ | |
| 45 | 6-I | 2'-Me, 4'-O-(3-Cl-5-CF₃-pyridin-2-yl) | —CH(Me)—CH₂—S—CH₂—SiMe₃ | |
| 46 | 3-I | 2'-Me, 4'-O-(3-Cl-5-CF₃-pyridin-2-yl) | —CH(Me)—CH₂—SO—CH₂—SiMe₃ | |
| 47 | 6-I | 2'-Me, 4'-O-(3-Cl-5-CF₃-pyridin-2-yl) | —CH(Me)—CH₂—SO—CH₂—SiMe₃ | |
| 48 | 3-I | 2'-Me, 4'-O-(3-Cl-5-CF₃-pyridin-2-yl) | —CH(Me)—CH₂—SO₂—CH₂—SiMe₃ | |
| 49 | 6-I | 2'-Me, 4'-O-(3-Cl-5-CF₃-pyridin-2-yl) | —CH(Me)—CH₂—SO₂—CH₂—SiMe₃ | |
| 50 | 3-I | 2'-Me, 4'-O-(3-Cl-5-CF₃-pyridin-2-yl) | —C(Me)₂—CH₂—S—CH₂—SiMe₃ | |
| 51 | 6-I | 2'-Me, 4'-O-(3-Cl-5-CF₃-pyridin-2-yl) | —C(Me)₂—CH₂—S—CH₂—SiMe₃ | |
| 52 | 3-I | 2'-Me, 4'-O-(3-Cl-5-CF₃-pyridin-2-yl) | —C(Me)₂—CH₂—SO—CH₂—SiMe₃ | |

-continued

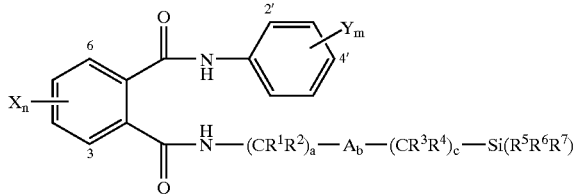

| No. | X | Y | —(CR¹R²)ₐ—Aᵦ—(CR³R⁴)꜀—Si(R⁵R⁶R⁷) | log P (pH 2.3) |
|---|---|---|---|---|
| 53 | 6-I | 2'-Me, 4'-—O—(3-Cl, 5-CF₃-pyridin-2-yl) | —C(Me)₂—CH₂—SO—CH₂—SiMe₃ | |
| 54 | 3-I | 2'-Me, 4'-—O—(3-Cl, 5-CF₃-pyridin-2-yl) | —C(Me)₂—CH₂—SO₂—CH₂—SiMe₃ | |
| 55 | 6-I | 2'-Me, 4'-—O—(3-Cl, 5-CF₃-pyridin-2-yl) | —C(Me)₂—CH₂—SO₂—CH₂—SiMe₃ | |

Preparation of the Starting Materials

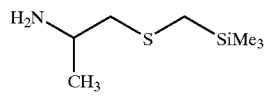

1.66 g (13.8 mmol) of trimethylsilylmethanethiol are initially charged at 0° C. in 20 ml of methanol. 0.788 g (13.8 mmol) of 2-methylaziridine is added dropwise, the mixture is stirred at 0° C. for another 4 h and then heated at reflux for 8 h, and the reaction mixture is subsequently concentrated under reduced pressure.

| Yield: | 1.84 g (48% of theory) of 1-{[(trimethylsilyl)-methyl]sulphanyl}-2-propanamide as an oil |
|---|---|
| HPLC: | log P (pH 2.3) = 1.28 |
| ¹H-NMR (CD₃CN): | δ = 0.05 (9H), 1.15 (d, 3H), 1.75 (q, 2H), 2.50 (m, 2H), 2.85 (br, 2H), 3.10 (m, 1H) ppm. |

The stated logP values were determined in accordance with EEC directive 79/831 Annex V.A8 by HPLC (High Performance Liquid Chromatography) using a reversed-phase column (C 18). Temperature: 43° C.

In the acidic range, the determination was carried out at pH 2.3 using the mobile phases 0.1% aqueous phosphoric acid and acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones.

The lambda max values were determined in the maxima of the chromatographic signals using the UV spectra from 200 nm to 400 nm.

Use Examples

Example A

*Heliothis virescens* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soybean shoots (*Glycine max*) are treated by being dipped into the preparation of active compound of the desired concentration and are populated with *Heliothis virescens* caterpillars while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE A

Plant-damaging insects
*Heliothis virescens* test

| Active compounds | Concentration of active compound in ppm | Kill rate in % after 7$^d$ |
|---|---|---|
| 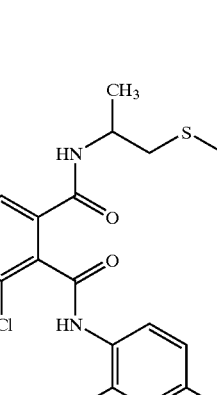 | 500 | 100 |
| 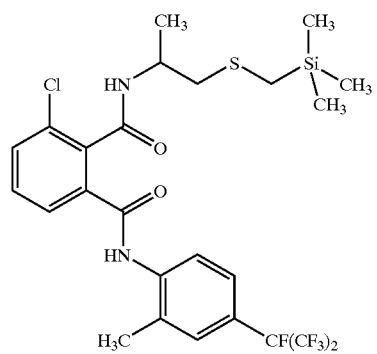 | 500 | 100 |
| 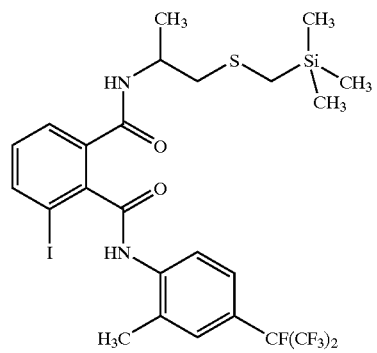 | 500 | 100 |

TABLE A-continued

Plant-damaging insects
*Heliothis virescens* test

| Active compounds | Concentration of active compound in ppm | Kill rate in % after 7$^d$ |
|---|---|---|
| 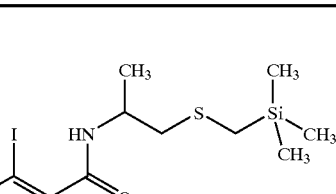 | 500 | 100 |

Example B

*Phaedon* Larvae Test

| | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity:

TABLE B

Plant-damaging insects
Phaedon larvae test

| Active compounds | Concentration of active compound in ppm | Kill rate in % after 7$^d$ |
| --- | --- | --- |
| (structure: 3-Cl benzene with two C(=O)NH groups; one NH connected to CH(CH₃)CH₂-S-CH₂-Si(CH₃)₃; other NH connected to 2-methyl-4-CF(CF₃)₂-phenyl) | 500 | 90 |
| (structure: 3-Cl benzene with two C(=O)NH groups; one NH connected to CH(CH₃)CH₂-S-CH₂-Si(CH₃)₃; other NH connected to 2-methyl-4-CF(CF₃)₂-phenyl) | 500 | 100 |
| (structure: 3-I benzene with two C(=O)NH groups; one NH connected to CH(CH₃)CH₂-S-CH₂-Si(CH₃)₃; other NH connected to 2-methyl-4-CF(CF₃)₂-phenyl) | 500 | 100 |
| (structure: 3-I benzene with two C(=O)NH groups; one NH connected to CH(CH₃)CH₂-S-CH₂-Si(CH₃)₃; other NH connected to 2-methyl-4-(4-CF₃-phenoxy)-phenyl) | 500 | 100 |

TABLE B-continued

Plant-damaging insects
Phaedon larvae test

| Active compounds | Concentration of active compound in ppm | Kill rate in % after 7$^d$ |
|---|---|---|
| 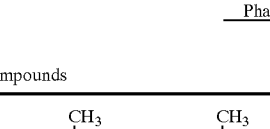 | 500 | 100 |

Example C
*Plutella* Test, Sensitive Strain

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*, sensitive strain) while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE C

Plant-damaging insects
Plutella test, sensitive strain

| Active compounds | Concentration of active compound in ppm | Kill rate in % after 7$^d$ |
|---|---|---|
| 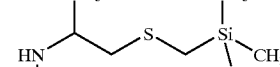 | 500 | 100 |
| 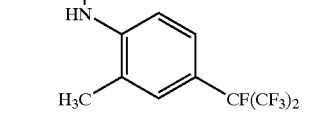 | 500 | 100 |
| 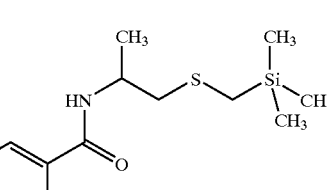 | 500 | 100 |
| 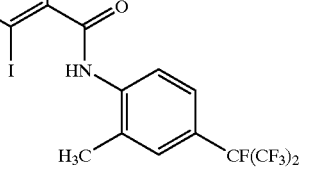 | 500 | 100 |

TABLE C-continued

Plant-damaging insects
Plutella test, sensitive strain

| Active compounds | Concentration of active compound in ppm | Kill rate in % after 7$^d$ |
|---|---|---|
| 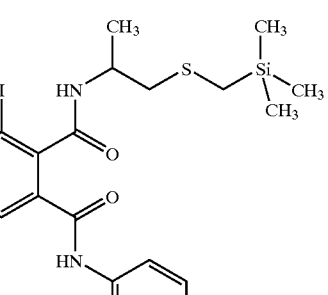 | 500 | 100 |

Example D

*Plutella* Test, Resistant Strain

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*, resistant strain) while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE D

Plant-damaging insects
Plutella test, resistant strain

| Active compounds | Concentration of active compound in ppm | Kill rate in % after 7$^d$ |
|---|---|---|
| (structure with CH₃, S, Si(CH₃)₃, Cl, HN, CF(CF₃)₂) | 500 | 100 |
| (structure with CH₃, S, Si(CH₃)₃, Cl, HN, CF(CF₃)₂) | 500 | 100 |

Example E

*Spodoptera exigua* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera exigua*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE E

Plant-damaging insects
*Spodoptera exigua* test

| Active compounds | Concentration of active compound in ppm | Kill rate in % after 7$^d$ |
|---|---|---|
| 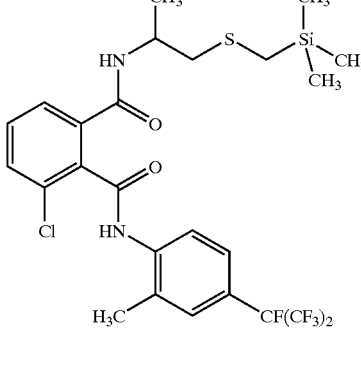 | 500 | 100 |
| 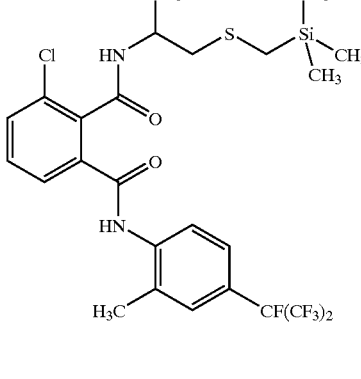 | 500 | 100 |
| 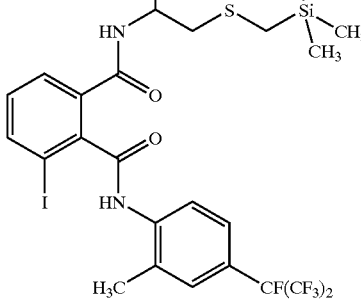 | 500 | 100 |

TABLE E-continued

Plant-damaging insects
*Spodoptera exigua* test

| Active compounds | Concentration of active compound in ppm | Kill rate in % after 7$^d$ |
|---|---|---|
| 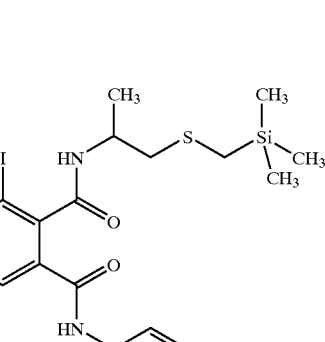 | 500 | 100 |

Example F

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples show good activity:

TABLE F
Plant-damaging insects
*Spodoptera frugiperda* test
| Active compounds | Concentration of active compound in ppm | Kill rate in % after 7[d] |
|---|---|---|
| 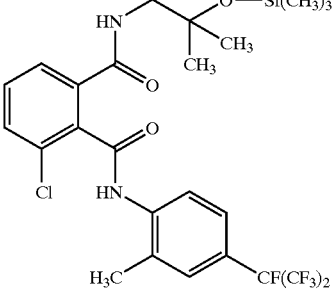 | 500 | 100 |
| 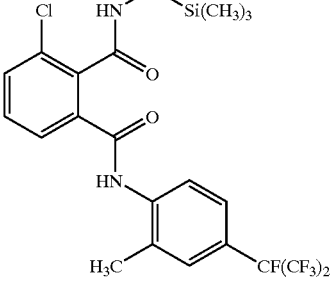 | 500 | 100 |
| 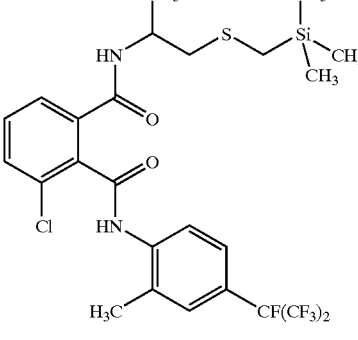 | 500 | 100 |
| 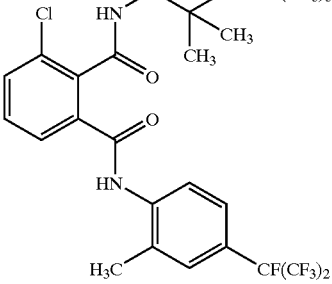 | 500 | 100 |

TABLE F-continued
Plant-damaging insects
Spodoptera frugiperda test
| Active compounds | Concentration of active compound in ppm | Kill rate in % after 7$^d$ |
|---|---|---|
| 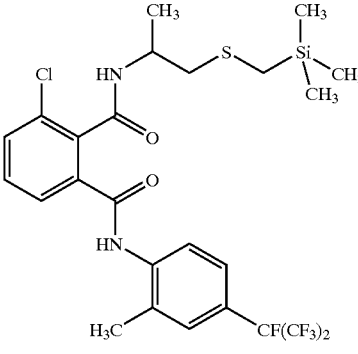 | 500 | 100 |
| 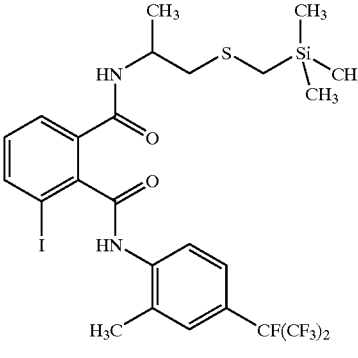 | 500 | 100 |
| 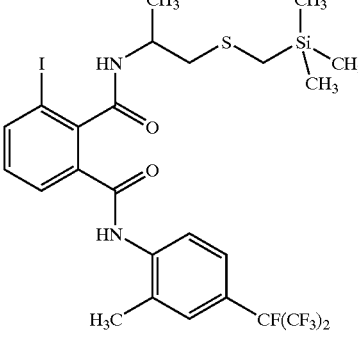 | 500 | 100 |
| 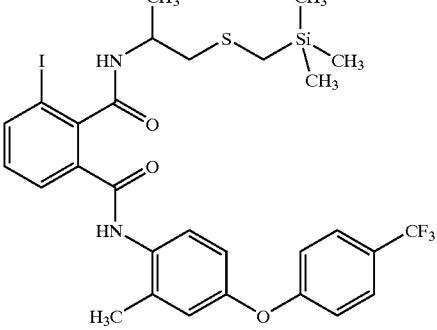 | 500 | 100 |

TABLE F-continued

Plant-damaging insects
*Spodoptera frugiperda* test

| Active compounds | Concentration of active compound in ppm | Kill rate in % after 7$^d$ |
| --- | --- | --- |
| [structure: 3-Cl, 2-methylphenyl diamide with trimethylsilylmethylthio propylamine and 4-(4-trifluoromethylphenoxy)-2-methylphenyl group] | 500 | 100 |
| [structure: 3-I analog with trimethylsilylmethylthio propylamine and 4-(4-trifluoromethylphenoxy)-2-methylphenyl group] | 500 | 100 |
| [structure: 3-Cl analog with trimethylsilylmethylthio propylamine and 4-(4-trifluoromethylphenoxy)-2-methylphenyl group] | 500 | 100 |
| [structure: 3-I analog with trimethylsilylmethylthio propylamine and 2-methyl-4-(2-tert-butyltetrazol-5-yl)phenyl group] | 500 | 100 |

Example G
*Diabrotica balteata* Test (Larvae in Soil)
Critical Concentration Test/Soil Insects—Treatment of Transgenic Plants

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example H
*Heliothis virescens* Test (Treatment of Transgenic Plants)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco budworm caterpillar *Heliothis virescens* while the leaves are still moist.

After the desired period of time, the kill in % is determined. 100% means that all caterpillars have been killed; 0% means that none of the caterpillars have been killed.

What is claimed is:

1. A phthalamide of formula (I)

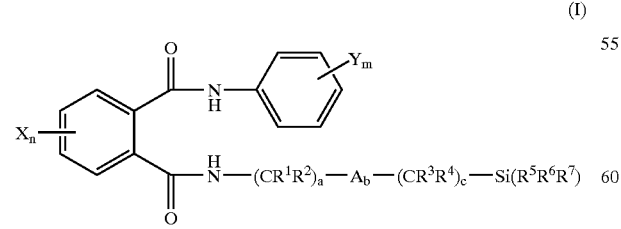

(I)

in which
X and Y independently of one another represent hydrogen, halogen, cyano, nitro, alkyl, halogenoalkyl, alkoxy, halogenoalkoxy, cycloalkyl, halogenocycloalkyl, cycloalkyloxy, halogenocycloalkyloxy, —S(O)$_d$-alkyl, or —S(O)$_d$-halogenoalkyl or represent optionally substituted phenyl, phenoxy, heteroaryl, or heteroaryloxy, n represents 1, 2, 3 or 4, m represents 1, 2, 3, 4, or 5, $R^1$, $R^2$, $R^3$, and $R^4$ independently of one another represent, hydrogen, alkyl, halogenoalkyl, or cycloalkyl, $R^5$, $R^6$, and $R^7$ independently of one another represent alkyl or alkoxy, A represents —S(O)$_d$— or oxygen, a represents 1, 2, 3, or 4, with the proviso that each repeat unit —CR$^1$R$^2$— can have identical or different meanings when a represents 2, 3, or 4, b represents 0 or 1, c represents 0, 1, 2, 3, or 4, with the proviso that each repeat unit —CR$^3$R$^4$— can have identical or different meanings when c represents 2, 3, or 4, d represents 0, 1, or 2.

2. A phthalamide of formula (I) according to claim 1 in which
X and Y independently of one another represent hydrogen, halogen, cyano, nitro, C$_1$–C$_6$-alkyl, C$_1$–C$_6$-halogenoalkyl, C$_1$–C$_6$-alkoxy, C$_1$–C$_6$-halogenoalkoxy, C$_3$–C$_6$-cycloalkyl, C$_3$–C$_6$-halogenocycloalkyl, C$_3$–C$_6$-cycloalkyloxy, halogenocycloalkyloxy, —S(O)$_d$—C$_1$–C$_6$-alkyl, or —S(O)$_d$—C$_1$–C$_6$-halogenoalkyl or represent phenyl, phenoxy, heteroaryl, or heteroaryloxy, each of which phenyl, phenoxy, heteroaryl, or heteroaryloxy is optionally mono- to tetra-substituted by identical or different substituents selected from the group consisting of halogen, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, and C$_1$–C$_6$-halogenoalkylthio, n represents 1, 2, or 3, m represents 1, 2, 3, or 4, $R^1$, $R^2$, $R^3$, and $R^4$ independently of one another represent hydrogen, C$_1$–C$_6$-alkyl, C$_1$–C$_6$-halogenoalkyl, or C$_3$–C$_6$-cycloalkyl, $R^5$, $R^6$, and $R^7$ independently of one another represent C$_1$–C$_6$-alkyl or C$_1$–C$_6$-alkoxy, A represents —S(O)$_d$— or oxygen, a represents 1, 2, 3, or 4, with the proviso that each repeat unit —CR$^1$R$^2$— can have identical or different meanings when a represents 2, 3, or 4, b represents 0 or 1, c represents 0, 1, 2, 3, or 4, with the proviso that each repeat unit —CR$^3$R$^4$— can have identical or different meanings when c represents 2, 3, or 4, d represents 0, 1 or 2.

3. A phthalamide of formula (I) according to claim 2 in which
X and Y independently of one another represent hydrogen, halogen, cyano, nitro, C$_1$–C$_6$-alkyl, C$_1$–C$_6$-halogenoalkyl, C$_1$–C$_6$-alkoxy, C$_1$–C$_6$-halogenoalkoxy, C$_3$–C$_6$-cycloalkyl, C$_3$–C$_6$-halogenocycloalkyl, C$_3$–C$_6$-cycloalkyloxy C$_3$–C$_6$-halogenocycloalkyloxy, —S(O)$_d$—C$_1$–C$_6$-alkyl, or —S(O)$_d$—C$_1$–C$_6$-halogenoalkyl or represent phenyl, phenoxy, heteroaryl or heteroaryloxy, each of which phenyl, phenoxy, heteroaryl or heteroaryloxy is mono- to tetrasubstituted by identical or different substituents selected from the group consisting of halogen, $C_1$–$C_6$-alkyl, and $C_1$–$C_6$-halogenoalkyl, and n, m, $R^1$, $R^2$, $R^3$, $R^4$, $R^5$, $R^6$, $R^7$, A, a, b, c, and d have the meanings given for formula (I) in claim 2.

4. A phthalamide of formula (I) according to claim 1 in which

X represents hydrogen, fluorine, chlorine, bromine, iodine, cyano, nitro, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_3$–$C_6$-cycloalkyl, —S(O)$_d$—$C_1$–$C_4$-alkyl, or —S(O)$_d$—$C_1$–$C_4$-halogenoalkyl having 1 to 9 fluorine, chlorine, and/or bromine atoms, Y represents hydrogen, fluorine, chlorine, bromine, iodine, cyano, nitro, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_3$–$C_6$-cycloalkyl, —S(O)$_d$—$C_1$–$C_4$-alkyl, or —S(O)$_d$—$C_1$–$C_4$-halogenoalkyl having 1 to 9 fluorine, chlorine, and/or bromine atoms; or represents phenyl, phenoxy, or 5- or 6-membered heteroaryl or heteroaryloxy having 1 to 4 heteroatoms comprising 0 to 4 nitrogen atoms, 0 to 2 nonadjacent oxygen atoms, and/or 0 to 2 nonadjacent sulphur atoms, each of which is optionally mono- to tetrasubstituted by identical or different substituents selected from the group consisting of fluorine, chlorine, bromine, iodine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms, n represents 1 or 2, m represents 1, 2, or 3, $R^1$, $R^2$, $R^3$, and $R^4$ independently of one another represent hydrogen, $C_1$–$C_4$-alkyl, $C_1$–$C_4$-halogenoalkyl having 1 to 9 fluorine, chlorine, and/or bromine atoms or $C_3$–$C_6$-cycloalkyl, $R^5$, $R^6$, and $R^7$ independently of one another represent $C_1$–$C_3$-alkyl or $C_1$–$C_3$-alkoxy, A represents —S(O)$_d$— or oxygen, a represents 1, 2, or 3, with the proviso that each repeat unit —CR$^1$R$^2$— can have identical or different meanings when a represents 2 or 3, b represents 0 or 1, c represents 0, 1, 2, or 3, with the proviso that each repeat unit —CR$^3$R$^4$— can have identical or different meanings when c represents 2 or 3, d represents 0, 1, or 2.

5. A phthalamide of formula (I) according to claim 4 in which the 5- or 6-membered heteroaryl or heteroaryloxy group is furyl, furyloxy, thienyl, thienyloxy, pyrrolyl, pyrrolyloxy, tetrazolyl, pyridyl, pyndyloxy, pyrimidinyl, pyrimidinyloxy, pyridazinyl, pyridazinyloxy, pyrazinyl, or pyrazinyloxy, each of which is optionally mono- to tetrasubstituted by identical or different substituents selected from the group consisting of fluorine, chlorine, bromine, iodine, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine, and/or bromine atoms, $C_1$–$C_4$-alkylthio, and $C_1$–$C_4$-halogenoalkylthio having 1 to 9 fluorine, chlorine, and/or bromine atoms.

6. A phthalamide of formula (I) according to claim 4 in which

X and Y independently of one another represent hydrogen, fluorine, chlorine, bromine, iodine, cyano, nitro, $C_1$–$C_4$-alkyl, $C_1$–$C_4$-halogenoalkyl having 1 to 9 fluorine, chlorine, and/or bromine atoms, $C_1$–$C_4$-alkoxy, $C_1$–$C_4$-halogenoalkoxy having 1 to 9 fluorine, chlorine and/or bromine atoms, $C_3$–$C_6$-cycloalkyl, —S(O)$_d$—$C_1$–$C_4$-alkyl, or —S(O)$_d$—$C_1$–$C_4$-halogenoalkyl having 1 to 9 fluorine, chlorine, and/or bromine atoms, and n, m, $R^1$, $R^2$, $R^3$, $R^4$, $R^5$, $R^6$, $R^7$, A, a, b, c, and d having the meanings given for formula (I) in claim 4.

7. A phthalamide of formula (I) according to claim 1 in which

X represents chlorine, bromine, or iodine,

Y represents methyl, ethyl, n-propyl, isopropyl, trifluoromethyl, pentafluoroethyl, n-heptafluoropropyl, isoheptafluoropropyl, trifluoromethoxy, or —OCF$_2$CF$_2$H, or represents phenoxy, pyridinyloxy, or tetrazolyl, each of which is mono- to trisubstituted by identical or different substituents selected from the group consisting of fluorine, chlorine, bromine, iodine, methyl, ethyl, n-propyl, isopropyl, n-butyl, isobutyl, sec-butyl, tert-butyl, —CF$_3$, —CHF$_2$, —CClF$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, —OCF$_3$, —OCHF$_2$, —OCF$_2$CF$_2$H, —SCF$_3$, and —SCHF$_2$, n represents 1, m represents 2, $R^1$, $R^2$, $R^3$, and $R^4$ independently of one another represent hydrogen, methyl, or ethyl, $R^5$, $R^6$, and $R^7$ independently of one another represent methyl, ethyl, methoxy, or ethoxy, A represents —S(O)$_d$— or oxygen, a represents 1, 2, or 3, with the proviso that each repeat unit —CR$^1$R$^2$— can have identical or different meanings when a represents 2 or 3, b represents 0 or 1, c represents 0, 1, or 2, with the proviso that each repeat unit —CR$^3$R$^4$— can have identical or different meanings when c represents 2, d represents 0, 1, or 2.

8. A phthalamide of formula (I) according to claim 7 in which

Y represents methyl, ethyl, n-propyl, isopropyl, trifluoromethyl, pentafluoroethyl, n-heptafluoropropyl, isoheptafluoropropyl, trifluoromethoxy, or —OCF$_2$CF$_2$H, and X, n, m, $R^1$, $R^2$, $R^3$, $R^4$, $R^5$, $R^6$, $R^7$, A, a, b, c, and d have the meanings given for formula (I) in claim 7.

9. A phthalamide of formula (I-a)

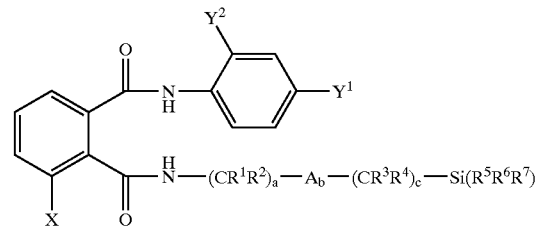

(I-a)

in which
  $Y^1$ and $Y^2$ independently of one another represent hydrogen, halogen, cyano, nitro, alkyl, halogenoalkyl, alkoxy, halogenoalkoxy, cycloalkyl, halogenocycloalkyl, cycloalkyloxy, halogenocycloalkyloxy, —S(O)$_d$-alkyl, or —S(O)$_d$-halogenoalkyl or represent optionally substituted phenyl, phenoxy, heteroaryl, or heteroaryloxy,
  A represents sulphur or oxygen,
  b represents 0 or 1, and
  X, $R^1$, $R^2$, $R^3$, $R^4$, $R^5$, $R_6$, $R^7$, a, and c have the meanings given for formula (I) in claim 1.

10. A phthalamide of formula (I-b)

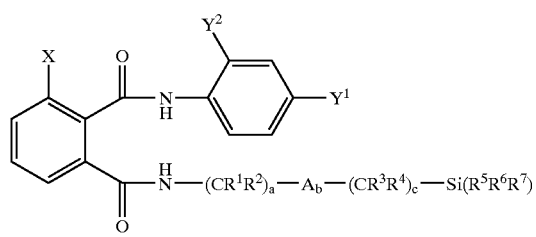

(I-b)

in which
  $Y^1$ and $Y^2$ independently of one another represent hydrogen, halogen, cyano, nitro, alkyl, halogenoalkyl, alkoxy, halogenoalkoxy, cycloalkyl, halogenocycloalkyl, cycloalkyloxy, halogenocycloalkyloxy, —S(O)$_d$-alkyl, or —S(O)$_d$-halogenoalkyl or represent optionally substituted phenyl, phenoxy, heteroaryl, or heteroaryloxy,
  A represents sulphur or oxygen,
  b represents 0 or 1, and
  X, $R^1$, $R^2$, $R^3$, $R^4$, $R^5$, $R^6$, $R^7$, a, and c have the meanings given for formula (I) in claim 1.

11. A phthalamide of formula (I-a) according to claim 9 in which represents SO or SO$_2$.

12. A phthalamide of formula (I-b) according to claim 10 in which represents SO or SO$_2$.

13. A phthalamide of formula (I-a) according to claim 9 in which $Y^1$ represents $C_1$–$C_4$-alkyl.

14. A phthalamide of formula (I-a) according to claim 9 in which $Y^1$ represents trifluoromethyl, pentafluoroethyl, n-heptafluoropropyl, or isoheptafluoropropyl.

15. A phthalamide of formula (I-b) according to claim 10 in which $Y^1$ represents $C_1$–$C_4$-alkyl.

16. A phthalamide of formula (I-b) according to claim 10 in which $Y^1$ represents trifluoromethyl, pentafluoroethyl, n-heptafluoropropyl, or isoheptafluoropropyl.

17. A phthalamide of formula (I-a) according to claim 9 in which $Y^2$ represents methyl.

18. A phthalamide of formula (I-b) according to claim 10 in which $Y^2$ represents methyl.

19. A phthalamide of formula (I) according to claim 1 in which $R^5$, $R^6$, and $R^7$ each represent methyl.

20. A phthalamide of formula (I) according to claim 1 in which A represents S, SO, or SO$_2$.

21. A phthalamide of formula (I) according to claim 1 selected from the group consisting of 3-chloro-$N^2$-{2-methyl-4-[1,2,2,2-tetrafluoro-1-(trifluoromethyl)ethyl]phenyl}-$N^1$-(1-methyl-2-{[(trimethylsilyl)methyl]sulphanyl}ethyl)phthalamide, 3-chloro-$N^1$-{2-methyl-4-[1,2,2,2-tetrafluoro-1-(trifluoromethyl)ethyl]phenyl}-$N^2$-(1-methyl-2-{[(trimethylsilyl)methyl]sulphanyl}ethyl)phthalamide, 3-chloro-$N^1$-[2-methyl-4-(1,1,2,2-tetrafluoroethoxy)phenyl]-$N^2$-[(trimethylsilyl)methyl]phthalamide 3-chloro-$N^2$-[2-methyl-4-(1,1,2,2-tetrafluoroethoxy)phenyl]-$N^1$-[(trimethylsilyl)methyl]phthalamide, 3-chloro-$N^1$-{2-methyl-4-[1,2,2,2-tetrafluoro-1-(trifluoromethyl)ethyl]phenyl}-$N^2$-{2-methyl-2-[(trimethylsilyl)oxy]propyl}phthalamide, and 3-chloro-$N^2$-{2-methyl-4-[1,2,2,2-tetrafluoro-1-(trifluoromethyl)ethyl]phenyl}-$N^1$-{2-methyl-2-[(trimethylsilyl)oxy]propyl}phthalamide.

22. A process for preparing a compound of the formula (I) according to claim 1 comprising reacting an imide of formula (II)

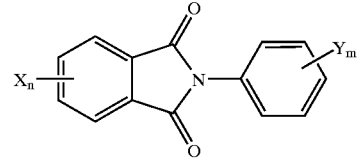

(II)

in which
  X, Y, n, and m have the meanings given for formula (I) in claim 1, with a silylamine of formula (III)

$$H_2N—(CR^1R^2)_a—A_b—(CR^3R^4)_c—Si(R^5R^6R^7)$$ (III)

in which
  $R^1$, $R^2$, $R^3$, $R^4$, $R^5$, $R^6$, $R^7$, A, a, b, and c have the meanings give for formula (I) in claim 1,
optionally in the presence of a diluent.

23. A pesticide comprising an effective amount of at least on compound of formula (I) according to claim 1 in combination with extenders and/or surfactants.

24. A method for controlling pests comprising allowing an effective amount of a compound of formula (I) according to claim 1 to act on pests and/or their habitat.

25. A process for preparing a pesticides comprising mixing a compound of formula (I) according to claim 1 with one or more extenders and/or surfactants.

* * * * *